United States Patent [19]

Kinast et al.

[11] 4,405,714
[45] Sep. 20, 1983

[54] PRODUCTION OF N-SUBSTITUTED DERIVATIVES OF 1-DESOXYNOJIRIMICIN

[75] Inventors: Günther Kinast; Michael Schedel; Wolfgang Koebernick, all of Wuppertal, Fed. Rep. of Germany

[73] Assignee: Bayer Aktiengesellschaft, Leverkusen, Fed. Rep. of Germany

[21] Appl. No.: 305,656

[22] Filed: Sep. 25, 1981

[30] Foreign Application Priority Data

Oct. 15, 1980 [DE] Fed. Rep. of Germany ....... 3038901

[51] Int. Cl.³ .................... C12P 19/26; C07D 211/46
[52] U.S. Cl. .................................... 435/84; 546/242
[58] Field of Search ........................ 435/84; 546/242

[56] References Cited

U.S. PATENT DOCUMENTS 4,246,345 1/1981 Kinast et al. ......................... 435/84
4,266,025 5/1981 Kinast et al. ......................... 435/84

OTHER PUBLICATIONS

The Peptides, vol. 1, Gross et al., editors, pp. 42–44 (1979).

*Primary Examiner*—Lionel M. Shapiro
*Attorney, Agent, or Firm*—Sprung, Horn, Kramer & Woods

[57] ABSTRACT

A process has been developed for the preparation of compounds of the formula

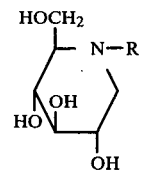

wherein R is hydrogen or an optionally substituted alkyl radical, which comprises reacting glucose with a compound of the formula $H_2N$-R wherein R has the meaning given above to form a 1-amino-sorbitol of the formula

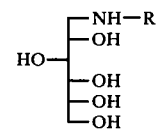

wherein
  R has the meaning given above,
reacting said 1-aminosorbitol with a compound providing a protective group which can be split off under acid conditions and is stable in the subsequent microbiological oxidation process, aerobically oxidizing the compound thus obtained microbiologically to give a protected 6-aminosorbose, splitting off the protective group under acid conditions and hydrogenating the 6-aminosorbose salt thus obtained either after being isolated or in one operation, to give the compound of the formula (I). The products obtained by the process of the invention are useful as α-glucoside inhibitors.

9 Claims, No Drawings

PRODUCTION OF N-SUBSTITUTED DERIVATIVES OF 1-DESOXYNOJIRIMICIN

The present invention relates to an unobvious process for the preparation of a certain known compound of the formula

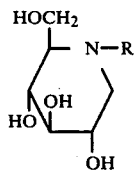
(I)

wherein R denotes a hydrogen atom or an optionally substituted alkyl radical.

It is known that the compounds of the formula (I) are very good α-glucosidase inhibitors, and are suitable as agents for use against diabetes (see European Published Patent Application No. 947).

A process for the preparation of 1-desoxynojirimicin (a compound of formula (I) in which R=H) in which 1-aminosorbitol of formula (II) is oxidised microbiologically to give 6-aminosorbose of formula (III), which is then hydrogenated to give the 1-desoxynojirimicin of formula (I) (R=H) is known from DE-OS (German Published Specification ) No. 2,834,122, corresponding to U.S. Pat. No. 4,246,345.

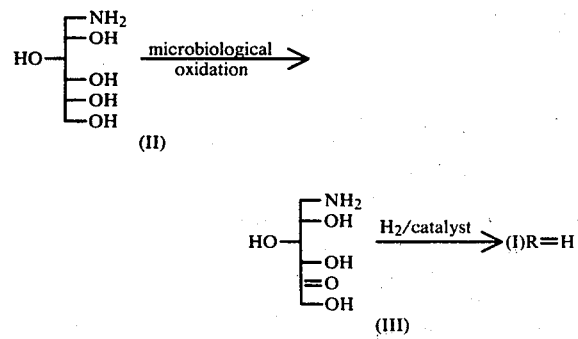

However, the yields of this process, in particular the volume yields in the microbiological reaction, are not yet optimal.

It is known, from European Published Patent Application No. 12 278 corresponding to U.S. Pat. No. 4,266,025, that the compounds of the formula (I) are obtained when the aminosorbitols of the formula (IV) wherein R is defined as in formula (I), are protected by a protective group (X) which can be split off by hydrogenolysis and is stable in the subsequent microbiological oxidation process, the resulting compounds of formula (V) are oxidised microbiologically to give the protected 6-aminosorboses of formula (VI) and the protective group is then split off by hydrogenolysis and the ring is closed to form the compounds of the formula (I)

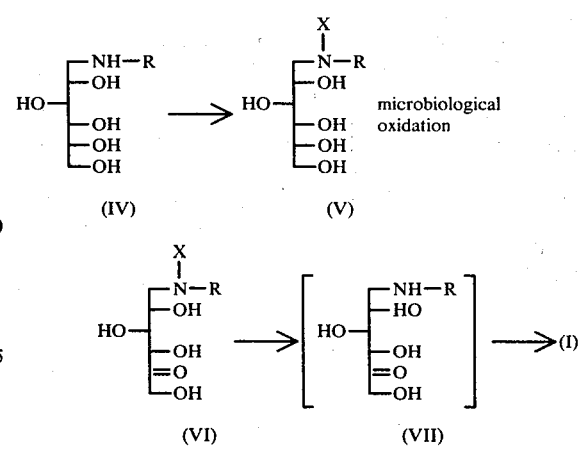

However, a relatively large amount of catalyst is required in the hydrogenation step of this process. In addition, the 6-amino-sorboses of formula (VII) formed as intermediate products in this process cannot be isolated as such.

Compounds of the formula (VII) are important as α-glucosidase inhibitors (see DE-OS (German Published Specification) No. 2,830,457 and DE-OS (German Published Specification) No. 2,830,424) and as intermediate products for the preparation of desoxynojirimicins of the formula (IX) (see European Published Patent Application No. 9 633 corresponding to U.S. Ser. No. 71,347, filing date Aug. 30, 1979, now U.S. Pat. No. 4,278,683, issued July 14, 1981):

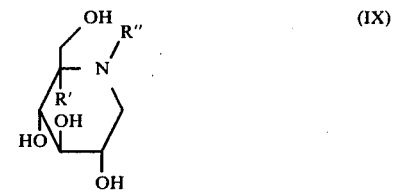

Further processes for the preparation of the compounds of the formula (I) are cited in European Published Patent Application No. 12 278 and are listed in European Published Patent Application No. 947. The synthesis processes described in these patent applications all proceed via several time-consuming stages, in which expensive purification steps are necessary.

It has now been found that the compounds of the formula (I) can be obtained by a simple route and in high yields, it being possible for the 6-amino-sorboses of formula (VII) to be isolated as highly pure intermediate products and it not being necessary to use large amounts of catalyst.

According to the present invention there is provided a process for the production of a compound of formula (I), as defined above, in which glucose is converted into a 1-aminosorbitol of the formula

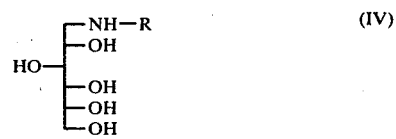

in which R has the meaning given in the definition of formula (I), the amino group thereof is then protected by introducing a protective group which can be split off under acid conditions and is stable in the subsequent microbiological oxidation process, the compounds thus prepared are oxidised microbiologically to give a protected 6-aminosorbose, the protective group is then split off under acid conditions and the 6-aminosorbose salt thus obtained is hydrogenated, either after being isolated or in one operation, to give the compound of the formula (I).

The process according to the present invention is described by the following reaction scheme:

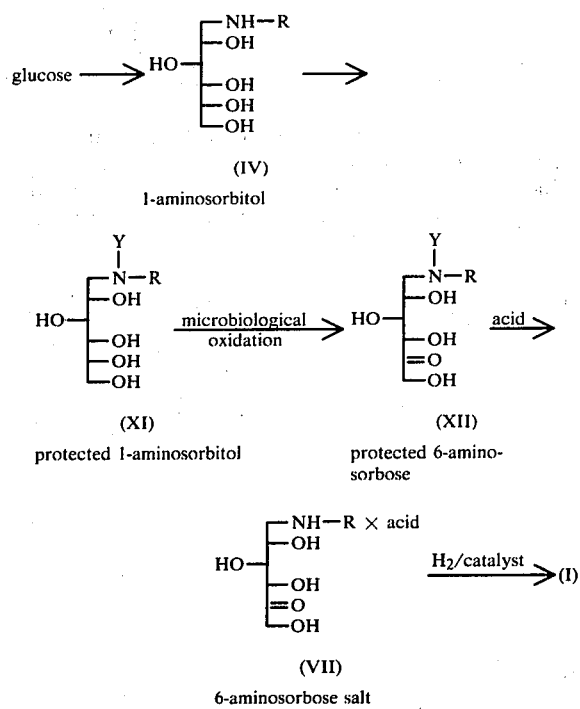

The radical R preferably denotes a hydrogen atom or a $C_1$ to $C_{10}$ (especially $C_1$–$C_4$) alkyl radical which is optionally substituted by OH or $C_1$ to $C_4$ alkoxy or by optionally substituted phenyl, wherein the optional substituent of phenyl is —O-($C_1$–$C_4$-alkyl), $C_1$–$C_4$-alkyl, COOH or —$CO_2$($C_1$–$C_4$-alkyl).

R very particularly preferably denotes a hydrogen atom, a $C_1$ to $C_{10}$ alkyl radical or a hydroxyethyl radical.

Suitable protective groups Y which can be split off under acid conditions and are stable during the microbiological oxidation are, for example, the tert.-butoxycarbonyl radical, the formyl radical, the dichloroacetyl radical and the o-nitrosulphenyl radical, but other protective groups from the large number of protective groups which can be split off under acid conditions are in principle suitable for carrying out the process according to the invention.

Tert.-butoxy-carbonyl and o-nitrosulphenyl are very particularly preferred.

The tert.-butoxycarbonyl ("BOC") protective group is introduced into the compounds of the formula (IV) in a manner which is in itself known, for example with di-BOC-pyrocarbonate, for example in a mixture of water and a water-miscible solvent.

The microbiological oxidation of the compounds of the formula (XI) to give the compounds of the formula (XII) is carried out in a manner which is in itself known, such as is described in European Published Patent Application No. 12 278. In this process, it is advantageous for the compound of the formula (XI) to be fed in several portions to the bacterial culture broth, in each case after complete oxidation of the preceding addition. Particularly high volume yields can thereby be achieved.

Microorganisms which are suitable for carrying out the oxidation or from which active extracts for carrying out the oxidation can be obtained can be Procaryotae, that is to say bacteria, or Eucaryotae, for example fungi, which can in each case belong to the most diverse taxonomic group. The expert in the microbiological field can easily find suitable microorganisms by growing a relatively large number of aerobic or optionally aerobic microorganisms in an appropriate nutrient medium which contains a compound of the formula (XI) and examining their ability to catalyse the oxidation reaction according to the invention and to accumulate a supply of compounds of the formula (XII).

Microorganisms which can particularly be employed for the oxidation are, for example, bacteria of the order Pseudomonadales, and within this order especially representatives of the family Pseudomonadaceae, and in this family, above all, bacteria of the genus Gluconobacter. Bacteria from the group of coryneform bacteria, in particular those of the genus Corynebacterium, have also proved suitable. Finally, the oxidation can also be carried out with fungi, thus, for example, with yeasts of the order Endomycetales, in particular with those of the family Spermophthoraceae, and of these chiefly with representatives of the genus Metschnikowia.

Examples which may be mentioned are: *Gluconobacter oxidans* spp. suboxydans (DSM 50 049), *Glucobacter oxidans* ssp. suboxydans (DSM 2003), *Corynebacterium betae* (DSM 20 141) and *Metschnikowia pulcherima* (ATCC 20 515).

The DSM numbers give the numbers under which the microorganisms mentioned are deposited in the Deutsche Sammlung für Mikroorganismen (German Collection of Microorganisms), Göttingen. *Mitschnikowia pulcherrima* is deposited in the American Type Culture Collection, Rockville, Md., USA.

If the oxidation is carried out with intact microorganisms in a growing culture, solid, semi-solid or liquid nutrient media can be used. Aqueous liquid nutrient media are preferably used.

Culturing can take place in all the nutrient media which are known to be used for culturing microorganisms of the abovementioned groups and which contain the compound to be oxidised. The nutrient medium must contain assimilable sources of carbon and nitrogen, as well as mineral salts. Suitable assimilable sources of carbon and nitrogen are, above all, complex mixtures, such as are provided, in particular, by biological products of various origin, for example soya bean flour, cotton seed flour, lentil flour, pea flour, soluble and insoluble vegetable proteins, corn-steep liquor, yeast extract, peptones and meat extract. Additional possible sources of nitrogen are ammonium salts and nitrates, for example ammonium chloride, ammonium sulphate, sodium nitrate and potassium nitrate. The mineral salts which the nutrient medium should contain supply, for example, the following ions: $Mg^{++}$, $Na^+$, $K^+$, $Ca^{++}$, $NH_4^+$, $Cl^-$, $SO_4^{--}$, $PO_4^{---}$ and $NO_3^-$, and ions of the customary trace elements, such as, Cu, Fe, Mn, Mo, Zn, Co and Ni.

If these salts or trace elements are not present in sufficient amounts in the said complex nutrient medium constituents or in the water used, it is expedient appropriately to supplement the nutrient medium.

It has been found that it is possible to achieve a considerable shorting of the reaction time by adding compounds of the intermediary metabolism and other cell elements to the medium, thus, for example, aminoacids or compounds from the tricarboxylic acid cycle.

The protected 1-aminosorbitol of formula (XI) to be oxidised can be added to the base nutrient medium either by itself or as a mixture with one or more oxidisable compounds which can be used are primary alcohols, such as $C_1$–$C_4$-alkanols (for example ethanol), secondary alcohols, such as $C_3$–$C_5$-alkanols (for example isopropanol), polyols, such as $C_1$–$C_4$-alkane diols or triols (for example sorbitol or glycerol), aldehydes (for example glycoaldehyde), aldoses, (for example glucose), or gluconic acids.

If one or more of the compounds mentioned is added to the nutrient solution, the compound to be oxidised can be added either before the inoculation or at any desired later point in time between the early lag-phase and the later stationary growth phase. In such a case, the organism in question is pre-cultured on the particular oxidisable compounds added. A pH range between 2 and 10, preferably 4–8, is suitable for the oxidation. It is advantageous to buffer the culture in a range, for example using phosphate buffer or acetate buffer.

As is customary in fermentation technology, it is also possible to regulate the pH automatically by injecting a sterile organic or inorganic acid (for example sulphuric acid), or a sterile alkali (for example sodium hydroxide solution) into the culture solution at intervals.

As is general in microbiological processes, a foreign infections should be avoided in the culture media. The customary measures are taken for this, such as sterilisation of the nutrient media, of the culture vessels and of the air required for the aeration. The culture vessels can be sterilised, for example, by steam sterilisation or by dry sterilisation; air and the culture media can likewise be sterilised by steam, or also by filtration.

The nutrient media are inoculated by generally customary methods, for example via slant cultures or glass cultures. Culturing of the microorganisms takes place under aerobic conditions and can be carried out according to the generally customary methods, for example using shake cultures, for example in shaking flasks, cultures agitated by air or submersed cultures. The microorganisms are preferably cultured by the aerobic submerse process in aerated fermenters, for example in customary submersed fermentation tanks. It is possible for the microorganisms to be cultured continuously or discontinuously. The discontinuous procedure is preferred.

It is expedient to ensure that the microorganisms are brought into sufficient contact with oxygen and the nutrients. This can be effected by the generally customary methods, such as shaking and stirring.

If an undesired amount of foam is formed during culture of the microorganism, the customary chemical foam suppressants, for example liquid fats and oils, oil-in-water emulsions, paraffins, higher alcohols, such as octadecanol, silicone oils and polyoxyethylene or polyoxypropylene compounds, can be added. Foam can also be suppressed or eliminated with the aid of the customary mechanical devices.

The culture temperature can be between about 20° and about 45° C. The culture period can be varied greatly, the composition of the nutrient medium and the culture temperature, for example, being of importance.

The particular optimum conditions can easily be established by any expert in the microbiological field.

It has been found that an incubation period of between 3 hours and 7 days after the addition is generally necessary for complete reaction of the compounds to be oxidised which are added to the culture broth.

It is also possible to carry out the oxidation reaction which concentrated cell suspensions of suitable microorganisms. Concentrated cell suspensions are prepared as follows: the microorganisms in question are grown in a suitable nutrient solution and are then harvested, for example by centrifugation, and suspended in a smaller volume of the same nutrient solution or in salt or buffer solution, for example physiological saline solution, aqueous solutions of $KH_2PO_4$, Na acetate or maleate or simply in tap water or distilled water. The protected 1-aminosorbitol of formula (XI) to be oxidised is then added to such a cell suspension and the oxidation reaction is carried out under the conditions described above for growing cultures.

The advantage of this process is the shortening in the reaction time of the oxidation to a few hours which is made possible by the higher concentration of microorganisms.

It is furthermore possible to carry out the oxidation not only with growing cultures of microorganisms or with concentrated cell suspensions obtained therefrom, but also with extracts or extract fractions prepared from these bacteria. These extracts can be crude extracts, such as are obtained by conventional breaking down of microorganism cells. Methods of breaking down which can be used are: ultrasonic treatment, passage through a French pressure cell, trituration with quartz sand, incubation with lysing enzymes, antolysis or freezing and thawing several times.

If non-fractionated crude extracts are used for the oxidation, in principle the same reaction conditions as has been described for carrying out the oxidation with growing or dormant microorganism cells have proved advantageous.

If the oxidation is to be carried out with partially purified extract preparations (enzymes), the generally customary methods of protein chemistry can be applied to obtain such preparations, such as ultra-centrifugation, a precipitation reaction, ion exchange chromatography or adsorption chromatography, gel filtration or electrophoretic methods. To clarify the question of which of several fractions obtained by one of the methods mentioned is suitable for catalysis of the oxidation reaction according to the invention, an aliquot of the fraction is mixed, at a temperature between 20° and 45° C. and at a pH between 2 and 10, with the compound to be oxidised and the formation of the reaction product in the batch is investigated by thin layer chromatography. For carrying out the reaction with fractionated cell extracts, it may be necessary to introduce additional reactants into the batch, for example physiological or synthetic electron acceptors, for example $NAD^+$, $NADP^+$, methylene blue, dichlorophenolindophenol and tetrazolium salts. If it is necessary to add such additional reactants, these can be used either in substrate amounts, that is to say in concentrations which correspond to that of the compound to be oxidised which is employed, or in catalytic amounts, that is to say in concentrations which are significantly below the chosen concentration of the compound to be oxidised.

If, in the second case, it is to be ensured that the oxidation is carried out approximately quantitatively, a system which continuously regenerates the reactant which is present only in a catalytic amount must also be added to the reaction batch. This system can be, for example, an enzyme which, in the presence of oxygen or other oxidising agents, ensures re-oxidation of an electron acceptor reduced in the course of the oxidation.

In other respects, the same conditions as have been described above for oxidation in growing microorganism cultures or concentrated cell suspensions have also proved advantageous for carrying out the oxidation with fractionated cell extracts. In particular, a temperature range of 20° to 45° C. and a pH range of 2 to 10 also applies in this case. However, the amount of reaction product formed achieves its maximum within a shorter period of time. An incubation time of between 2 hours and 3 days is sufficient, depending on the extract concentration.

The formation of the desired compound in the culture medium as a function of time can be followed by thin layer chromatography.

The compounds of the formula (XII) are isolated in a manner which is in itself known, such as is described, for example, in European Published Patent Application No. 12278. In a particularly advantageous procedure, the compounds of the formula (XII) are allowed to crystallise out directly from the oxidation medium and are separated off and recrystallised from a suitable solvent (for example an alcohol, such as methanol).

To split off the protective groups, the appropriate blocked 6-amino-L-sorboses of formula (XII) are stirred in concentrated or dilute acid (for example hydrochloric acid) at room temperature and the progress of the splitting off reaction is followed by means of thin layer chromatography. After adding water-miscible organic solvents (for example n-propanol), the deblocked 6-amino-L-sorboses of formula (VII) can be isolated as the hydrochloride in crystalline form or in the form of a syrup. The resulting salts of the compounds of the formula (VII) are converted into the compounds of the formula (I) by hydrogenation in a manner which is in itself known (see European Published Patent Application No. 7040).

The hydrogenation is carried out in aqueous solution at room temperature and under an increased pressure of $H_2$ (for example $20 \times 10^5$ Pa). Suitable catalysts are noble metal catalysts (for example 5% strength Pt-on-charcoal), but Raney nickel is more advantageously employed.

The reaction steps for the process according to the present invention, following the conversion of glucose into 1-aminosorbitol, are illustrated by the following Examples.

EXAMPLE 1

Preparation of 1-tert.-butoxycarbonylaminosorbitol

To a solution of 90 g 1-amino-L-sorbitol in 1 l THF (tetrahydrofuran)/$H_2O$ 1:1 (v/v) 131 g of di-BOC-pyrocarbonat (BOC-anhydride) in 500 ml THF were added dropwise at room temperature. The mixture was stirred overnight, the tetrahydrofuran was evaporated off in vacuo, the aqueous phase was extracted twice with ethyl acetate and then evaporated to dryness and the residue was recrystallised from isopropanol.

Yield: 110 g, melting point: 86° to 88° C.

EXAMPLE 2

Preparation of 1-tert.-butoxycarbonylamino-N-methylsorbitol

The preparation was carried out analogously to that in Example 1, starting from 1-methylaminosorbitol.

Yield: 95%; melting point 78°–80° C.

EXAMPLE 3

Preparation of 1-tert.-butoxycarbonylamino-N-(β-hydroxyethyl)-sorbitol

The preparation was carried out analogously to that in Example 1, starting from 1-β-hydroxyethylaminosorbitol.

Yield 78%; Melting point 103°–104° C.

EXAMPLE 4

Oxidation of 1-tert.-butoxycarbonylaminosorbitol by *Gluconobacter oxidans* spp. *suboxidans* (DSM 50 049)

The conversion was carried out in the following nutrient solution: 20 g/liter of yeast extract, 50 g/liter of sorbitol and 4 g/liter of $KH_2PO_4$. The nutrient solution constituents were dissolved in demineralised water and the pH value was adjusted to 6.5 with NaOH. 250 ml portions of the nutrient solution were introduced into 1 liter conical flasks and the flasks were placed in an autoclave at 121° C. for 20 minutes. After cooling, 10 g/liter of 1-tert.-butoxycarbonylaminosorbitol were added under sterile conditions and the nutrient solution was inoculated to 5% strength with a preculture which had been grown in the same nutrient solution but without 1-tert.-butoxycarbonylaminosorbitol. Incubation took place at 28° C. on a rotary shaking machine at 280 rpm. The conversion was followed by means of thin layer chromatography.

Complete conversion of 10 g/liter was achieved after 96 hours. To isolate the 6-tert.-butoxycarbonylaminosorbose, the fermentation batch was extracted with butanol, the extract was concentrated in a rotary evaporator and the residue was recrystallised from ethyl acetate.

Melting point: 141° to 143° C.

EXAMPLE 5

Oxidation of 1-tert.-butoxycarbonylaminosorbitol by *Metschnikowia pulcherrima* (ATCC 20 515)

The microorganism *Metschnikowia pulcherrima* (ATCC 20 515) was precultured in slant tubes on a medium which contained, per liter, 3 g of yeast extract, 6 g of peptone, 10 g of glucose, 8 g of NaCl and 20 g of agar in demineralised water. 250 ml of liquid medium (in a 1 liter conical flask) which contained, per liter, 3 g of yeast extract, 6 g of peptone, 10 g of sorbitol, 8 g of NaCl and 10 g of 1-tert.-butoxycarbonylaminosorbitol, dissolved in demineralised water, and which had been sterilised in an autoclave by heating to 121° C. for 20 minutes, were inoculated with this preculture. The culture was incubated at 35° C. on a rotary shaking machine at 200 rpm. The 1-tert.-butoxycarbonylaminosorbose content in the culture broth was determined by thin layer chromatography. After 2 days, 3 g/liter (30%) had been converted. The fermentation was interrupted at this point in time.

EXAMPLE 6

Oxidation of 1-tert.-butoxycarbonylaminosorbitol by *Corynebacterium betae* (DSM 20 141)

The microorganism *Corynebacterium betae* (DSM 20 141) was precultured in slant tubes which contained the following nutrient media: 10 g/liter of tryptically digested casein peptone, 6 g/liter of yeast extract, 5 g/liter of sorbitol, 5 g/liter of NaCl and 20 g/liter of agar in demineralised water. 250 ml of liquid nutrient solution (in a 1 liter conical flask) which contained, per liter, 10 g of tryptically digested casein peptone, 5 g of yeast extract, 5 g of sorbitol, 5 g of NaCl and 10 g of 1-tert.-butoxycarbonylaminosorbitol were inoculated with a slant tube containing a well-grown culture. The nutrient medium constituents were dissolved in demineralised water and sterilised by heating to 121° C. in an autoclave for 20 minutes. The culture was incubated at 37° C. on a rotary shaking machine at 200 rpm.

The content of 1-tert.-butoxycarbonylaminosorbitose was determined by thin layer chromatography. After 2 days, 5 g/liter (corresponding to 50%) had been converted. At this point in time, the fermentation was interrupted.

EXAMPLE 7

Oxidation of 1-tert.-butoxycarbonylamino-N-methylsorbitol by *Glucobacter oxydans* ssp. *suboxydans* (DSM 2003)

A preculture of *Glucobacter oxydans* ssp. *suboxydans* (DSM 2003) was grown in the following nutrient solution: 200 g/liter of sorbitol, 40 g/liter of yeast extract and 10 g/liter of $KH_2PO_4$, dissolved in demineralised water. The pH value was adjusted to 6.5 with NaOH. 250 ml of this nutrient solution, which had been kept in an autoclave at 121° C. for 20 minutes, was inoculated from a slant tube and the batch was incubated at 28° C. on a rotary shaking machine at 280 rpm. After 36 hours, a fermenter which contained 10 liters of nutrient solution of the following composition was inoculated with this preculture: 100 g/liter of sorbitol, 20 g/liter of yeast extract, 5 g/liter of $KH_2PO_4$ and 1 ml of polyol antifoaming agent, dissolved in dermineralised water. The contents of the fermenter were sterilised at 121° C. for 30 minutes. The fermentation conditions were: stirring: 500 rpm, temperature: 30° C., aeration: 10 liters of air/minute; the pH value was kept constant at 5.8 by automatic addition of 5 N NaOH.

After 36 hours, 500 ml of a 20% strength hot solution, at 70° C., of 1-tert.-butoxycarbonylamino-N-methylsorbitol were added under sterile conditions. After 84 hours, complete conversion of 10 g/liter was achieved.

The oxidation product was isolated analogously to that in Example 4.

EXAMPLE 8

Oxidation of 1-tert.-butoxycarbonylamino-N-(β-hydroxyethyl)sorbitol by *Glucobacter oxydans* ssp. *suboxydans* (DSM 2003).

*Glucobacter oxydans* ssp. *suboxydans* (DSM 2003) was cultured in a 10 liter fermenter as described in Example 7. After 36 hours, 250 ml were introduced, under sterile conditions, into a 1 liter conical flask which contained 2.5 g of 1-tert.-butoxycarbonylamino-N-(β-hydroxyethyl)-sorbitol, which had been weighed into the flask under sterile conditions. The flask was incubated at 28° C. and 280 rpm. After 72 hours, complete conversion was achieved. The oxidation product was isolated analogously to that in Example 4, using n-butanol.

EXAMPLE 9

6-Amino-6-desoxy-L-sorbose hydrochloride 20 g of N-tert.-butoxycarbonyl-6-amino-6-desoxy-L-sorbose were introduced in portions into a mixture of 6.4 ml of $H_2O$ and 13.2 ml of concentrated hydrochloric acid, whilst stirring and cooling. The batch was subsequently stirred for 2 hours, without cooling, and 120 ml of n-propanol were then added in the course of 2 hours. The resulting suspension of crystals was then stirred at 0° C. for 1 hour and filtered on a suction filter. The crystals were washed with a little n-propanol and dried at room temperature in a vacuum drying cabinet.

Yield: 14.2 g ≙ 92% of theory.

Melting point: (decomposition): 116°–125° C.

| $C_6H_{13}NO_5 \times HCl$ (215.2) | |
|---|---|
| Calculated C 33.30% | Found C 33.25% |
| H 6.54% | H 6.68% |
| N 6.53% | N 6.46% |

The product could also crystallise as the monohydrate.

Melting point (decomposition): 70° to 75° C.; this material also gave satisfactory analysis values.

EXAMPLE 10

Desoxynojirimicin hydrochloride 100 g (0.47 mol) of 6-amino-6-desoxy-L-sorbose hydrochloride were dissolved in 1000 ml of water, 15 g of Raney nickel were added and hydrogenation was carried out for 3 hours at room temperature and under a $H_2$ pressure of $20 \times 10^5$ Pa. The autoclave was let down, the catalyst was filtered off and the resulting solution was evaporated in vacuo. The solid residue was dissolved in 40 ml of water under the influence of heat, and 400 ml of ethanol were then slowly added at 50° C. The suspension of crystals which was formed was cooled to −5° C. and filtered and the crystals were washed with a little ethanol. They were dried overnight in a vacuum drying cabinet at 50° C.

Yield: 70.5 g ≙ 75%.

Melting point: 208° to 210° C.

The resulting material was identical to an original sample (IR, HPLC).

EXAMPLE 11

6-Methylamino-6-desoxy-L-sorbose hydrochloride 8 g (0.027 mole) of N-tert.-butoxycarbonyl-6-methylamino-6-desoxy-L-sorbose were deblocked hydrolytically in a manner analogous to that in Example 9. 5 g of the syrupy hydrochloride, which was immediately further processed because of its readiness to decompose, were obtained.

Yield: 5 g = 80% of syrup.

EXAMPLE 12

N-Methyl-1-desoxynojirimicin 5 g of 6-methylamino-6-desoxy-L-sorbose hydrochloride were dissolved in 50 ml of $H_2O$, 0.5 g of 5% strength Pt-on-charcoal were added and hydrogenation was carried out for 3 hours at room temperature and under a H$_2$ pressure of 20.10$^5$ Pa. The filtered aqueous solution of the hydrochloride was freed from Cl$^-$ with a strongly basic ion exchanger and evaporated to dryness and the residue was crystallised from ethanol/H$_2$O 10:1.

2.3 g of the crystalline product were obtained.
Yield: 2.3 g ≙ 60% of theory.
Melting point: 152° to 154° C.

EXAMPLE 13

6-Hydroxyethylamino-L-sorbose hydrochloride 4 g (0.012 mol) of the BOC-protected 6-hydroxyethylamino-L-sorbose were reacted with 8 N hydrochloric acid in a manner analogous to that in Example 9, and 2.2 g of 6-hydroxyethylamino-L-sorbose hydrochloride were obtained as a syrup. The product was not characterised further, but was used immediately for the hydrogenation.

EXAMPLE 14

N-Hydroxyethyl-1-desoxynojirimicin 2.2 g of 6-hydroxyethylamino-L-sorbose hydrochloride were dissolved in 30 ml of water, 300 mg of 5% strength Pt-on-charcoal were added and hydrogenation was carried out for 3 hours at room temperature and under a H$_2$ pressure of 20.10$^5$ Pa. The catalyst was filtered off and the aqueous filtrate was freed from chloride with a strongly basic ion exchanger. The aqueous solution was evaporated in a rotary evaporator and the residue was crystallised from ethanol/H$_2$O 10:1.

Yield: 1 g 55% of theory.
Melting point: 144° to 146° C.

What is claimed is:

1. A process for the production of a compound of the formula

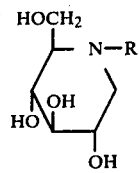 (I)

wherein
R denotes a hydrogen atom or an optionally substituted alkyl radical,
which comprises reacting glucose with a compound of the formula H$_2$N-R wherein R has the meaning given above to form a 1-amino-sorbitol of the formula

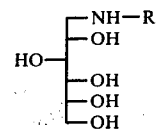 (IV)

wherein R has the meaning given above, reacting said 1-aminosorbitol with a compound providing a protective group which can be split off under acid conditions and is stable in the subsequent microbiological oxidation process, aerobically oxidizing the compound thus obtained microbiologically to give a protected 6-aminosorbose, splitting off the protective group under acid conditions and hydrogenating the 6-aminosorbose salt thus obtained either after being isolated or in one operation, to give the compound of the formula (I).

2. A process according to claim 1, characterized in that the radical R denotes a hydrogen atom or a C$_1$ to C$_{10}$ alkyl radical which is optionally substituted by OH or C$_1$-C$_4$-alkoxy or by optionally substituted phenyl.

3. A process according to claim 2, characterized in that the radical R denotes hydrogen, C$_1$-C$_{10}$-alkyl or a hydroxyethyl.

4. A process according to claim 2, characterized in that the radical R denotes hydrogen.

5. A process according to claim 2, characterized in that the radical R denotes methyl.

6. A process according to claim 2, characterized in that the radical R denotes hydroxyethyl.

7. A process according to claim 1, characterized in that the protective group is an acyl radical which can be split off under acid conditions or a sulphenyl radical which can be split off under acid conditions.

8. A process according to claim 7, characterized in that the protective group is tert.-butoxycarbonyl or o-nitrosulphenyl.

9. A process for the production of a compound of the formula

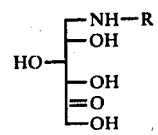 (VII)

wherein R has the meaning as defined in claim 1 which comprises treating a compound of the formula

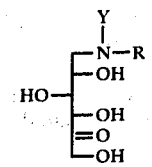 (XII)

wherein R has the meaning given above and Y is a protective group with an acid suitable for splitting off the protective group.

* * * * *